US011957422B2

(12) United States Patent
Tschudy et al.

(10) Patent No.: US 11,957,422 B2
(45) Date of Patent: Apr. 16, 2024

(54) SURGICAL INSTRUMENTS FOR USE IN ROBOTIC SURGICAL SYSTEMS AND METHODS RELATING TO THE SAME

(71) Applicant: Covidien LP, Mansfield, MA (US)

(72) Inventors: Christopher T. Tschudy, Arvada, CO (US); Samuel W. Tobey, Erie, CO (US)

(73) Assignee: Covidien LP, Mansfield, MA (US)

( * ) Notice: Subject to any disclaimer, the term of this patent is extended or adjusted under 35 U.S.C. 154(b) by 794 days.

(21) Appl. No.: 17/071,916

(22) Filed: Oct. 15, 2020

(65) Prior Publication Data
US 2022/0117679 A1    Apr. 21, 2022

(51) Int. Cl.
| | |
|---|---|
| *A61B 34/30* | (2016.01) |
| *B25J 9/04* | (2006.01) |
| *B25J 9/16* | (2006.01) |
| *B25J 15/00* | (2006.01) |

(52) U.S. Cl.
CPC .............. *A61B 34/30* (2016.02); *B25J 9/042* (2013.01); *B25J 9/1692* (2013.01); *B25J 15/0019* (2013.01)

(58) Field of Classification Search
CPC . A61B 34/30; A61B 2090/0803; A61B 34/25; A61B 34/00; B25J 9/042; B25J 9/1692; B25J 15/0019
See application file for complete search history.

(56) References Cited

U.S. PATENT DOCUMENTS

| | | | |
|---|---|---|---|
| 5,752,973 A | 5/1998 | Kieturakis | |
| 5,792,135 A | 8/1998 | Madhani et al. | |
| 5,848,986 A | 12/1998 | Lundquist et al. | |
| 6,817,974 B2 | 11/2004 | Cooper et al. | |
| 7,386,365 B2 | 6/2008 | Nixon | |
| 7,699,835 B2 | 4/2010 | Lee et al. | |

(Continued)

FOREIGN PATENT DOCUMENTS

| | | |
|---|---|---|
| EP | 3104324 A1 | 12/2016 |
| WO | 2012124831 A1 | 9/2012 |
| WO | 2020055707 A1 | 3/2020 |

OTHER PUBLICATIONS

International Search Report and Written Opinion issued in corresponding International Application No. PCT/US2021/050462 dated Jan. 17, 2022, 15 pages.

*Primary Examiner* — Robert T Nguyen
(74) *Attorney, Agent, or Firm* — Carter, DeLuca & Farrell LLP

(57) ABSTRACT

A surgical system includes at least one input coupler configured to receive an input, an end effector assembly, and an actuation assembly operably coupled between the at least one input coupler and the end effector assembly such that, in response receipt of the input by the at least one input coupler, the end effector assembly is manipulated. The system further includes a storage device storing setting information and adjustment information. The setting information enables determination of a first input to the at least one input coupler to achieve a desired manipulation of the end effector assembly. The adjustment information enables adjustment of the setting information for determination of a second input, different from the first input, to the at least one input coupler to achieve the desired manipulation of the end effector assembly.

13 Claims, 12 Drawing Sheets

(56) References Cited

U.S. PATENT DOCUMENTS

| | | |
|---|---|---|
| 7,799,028 B2 | 9/2010 | Schechter et al. |
| 7,861,906 B2 | 1/2011 | Doll et al. |
| 7,918,230 B2 | 4/2011 | Whitman et al. |
| 8,452,447 B2 | 5/2013 | Nixon |
| 8,579,176 B2 | 11/2013 | Smith et al. |
| 8,761,930 B2 | 6/2014 | Nixon |
| 9,014,856 B2 | 4/2015 | Manzo et al. |
| 9,055,961 B2 | 6/2015 | Manzo et al. |
| 9,085,083 B2 | 7/2015 | Nixon |
| 9,244,524 B2 | 1/2016 | Inoue et al. |
| 9,317,651 B2 | 4/2016 | Nixon |
| 9,408,668 B2 | 8/2016 | Durant et al. |
| 9,474,569 B2 | 10/2016 | Manzo et al. |
| 9,623,563 B2 | 4/2017 | Nixon |
| 9,664,262 B2 | 5/2017 | Donlon et al. |
| 9,675,354 B2 | 6/2017 | Weir et al. |
| 9,687,311 B2 | 6/2017 | Turner |
| 9,872,737 B2 | 1/2018 | Nixon |
| 9,913,694 B2 | 3/2018 | Brisson |
| 9,956,050 B2 | 5/2018 | Overmyer et al. |
| 9,968,412 B2 | 5/2018 | Overmyer et al. |
| 10,033,308 B2 | 7/2018 | Chaghajerdi et al. |
| 10,149,727 B2 | 12/2018 | Overmyer et al. |
| 10,155,316 B2 | 12/2018 | Wakai et al. |
| 10,194,992 B2 | 2/2019 | Robinson |
| 10,277,097 B2 | 4/2019 | Weir et al. |
| 10,327,773 B2 | 6/2019 | Weir et al. |
| 10,483,881 B2 | 11/2019 | Liao et al. |
| 10,595,946 B2 | 3/2020 | Nixon |
| 10,731,740 B1 | 8/2020 | Cui et al. |
| 10,751,051 B2 | 8/2020 | Weir et al. |
| 10,765,432 B2 | 9/2020 | Moore et al. |
| 10,765,486 B2 | 9/2020 | Bajo et al. |
| 10,765,487 B2 | 9/2020 | Ho et al. |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2006/0022015 A1 | 2/2006 | Shelton et al. |
| 2006/0025811 A1 | 2/2006 | Shelton |
| 2006/0161138 A1 | 7/2006 | Orban et al. |
| 2007/0233052 A1 | 10/2007 | Brock |
| 2008/0015631 A1 | 1/2008 | Lee et al. |
| 2008/0134812 A1 | 6/2008 | Murata |
| 2010/0274265 A1 | 10/2010 | Wingardner et al. |
| 2010/0292691 A1 | 11/2010 | Brogna |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2013/0123783 A1 | 5/2013 | Marczyk et al. |
| 2014/0276723 A1 | 9/2014 | Parihar et al. |
| 2017/0042560 A1 | 2/2017 | Lee et al. |
| 2017/0150975 A1 | 6/2017 | Bozung |
| 2017/0265951 A1 | 9/2017 | Grover et al. |
| 2017/0273749 A1 | 9/2017 | Grover et al. |
| 2017/0365923 A1 | 12/2017 | Schmutzler et al. |
| 2018/0028271 A1 | 2/2018 | Rockrohr |
| 2018/0071037 A1 | 3/2018 | Grover et al. |
| 2018/0116735 A1* | 5/2018 | Tierney .................. G16H 40/63 |
| 2019/0008600 A1 | 1/2019 | Pedros et al. |
| 2019/0099227 A1 | 4/2019 | Rockrohr |
| 2019/0274769 A1 | 9/2019 | Perdue et al. |
| 2020/0237453 A1 | 7/2020 | Anglese |
| 2020/0237455 A1 | 7/2020 | Anglese |
| 2020/0246058 A1 | 8/2020 | Traina |
| 2020/0253676 A1 | 8/2020 | Traina |
| 2020/0261166 A1 | 8/2020 | Anglese |
| 2020/0261167 A1 | 8/2020 | Anglese |
| 2020/0261168 A1 | 8/2020 | Anglese |
| 2022/0313349 A1* | 10/2022 | Lath .................... A61B 18/1442 |
| 2023/0131999 A1* | 4/2023 | Holbrook ................ A61B 34/20 |
| | | 606/206 |
| 2023/0354228 A1* | 11/2023 | Kim .................. H04W 56/0015 |

* cited by examiner

SURGICAL INSTRUMENTS FOR USE IN ROBOTIC SURGICAL SYSTEMS AND METHODS RELATING TO THE SAME

FIELD

The present disclosure relates to surgical instruments and, more specifically, to surgical instruments such as, for example, for use in robotic surgical systems, and methods relating to the same.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

SUMMARY

As used herein, the term "distal" refers to the portion that is being described which is further from an operator (whether a human surgeon or a surgical robot), while the term "proximal" refers to the portion that is being described which is closer to the operator. The terms "about," substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is a surgical system including at least one input coupler configured to receive an input, an end effector assembly, and an actuation assembly operably coupled between the at least one input coupler and the end effector assembly such that, in response receipt of the input by the at least one input coupler, the end effector assembly is manipulated. The surgical system further includes a storage device storing setting information and adjustment information. The setting information enables determination of a first input to the at least one input coupler to achieve a desired manipulation of the end effector assembly. The adjustment information enables adjustment of the setting information for determination of a second input, different from the first input, to the at least one input coupler to achieve the desired manipulation of the end effector assembly.

In an aspect of the present disclosure, the adjustment information is correlated with use information. The use information may include an amount of time and/or a number of events. The storage device may additionally or alternatively store the use information.

In another aspect of the present disclosure, the adjustment information is correlated with condition information. The condition information may include at least one of a presence of articulation or an amount of articulation.

In still another aspect of the present disclosure, the at least one input coupler is configured to receive a rotational input as the input and to rotate in response thereto.

In yet another aspect of the present disclosure, at least one motor is configured to provide the input to the at least one input coupler. In such aspects, a control device may be provided and configured to access the setting information and the adjustment information to control the motor based thereon to provide the first input or the second input to achieve the desired manipulation.

In still yet another aspect of the present disclosure, the control device is further configured to access at least one of use information or condition information and to control the motor based on the setting information, the adjustment information, and the at least one of the use information or condition information to provide the first input or the second input to achieve the desired manipulation.

A method provided in accordance with the present disclosure includes receiving an instruction to manipulate a surgical instrument, determining setting information associated with the instructed manipulation, determining adjustment information corresponding to the setting information, adjusting the setting information using the adjustment information, and providing an input to the surgical instrument based upon the adjusted setting information to achieve the instructed manipulation.

In an aspect of the present disclosure, the setting information is adjusted using the adjustment information and the adjustment information is correlated with additional information, e.g., use information (such as an amount of time and/or a number of events) and/or condition information (such as a presence of articulation and/or an amount of articulation).

In another aspect of the present disclosure, the method further includes receiving a second instruction to manipulate the surgical instrument, determining second setting information associated with the second instructed manipulation, and providing a second input to the surgical instrument based on the second setting information to achieve the second instructed manipulation. The second setting information may be unadjusted setting information. The instruction and manipulation may be prior to or after the second instruction and manipulation.

Another surgical system provided in accordance with aspects of the present disclosure includes a robotic surgical system, a surgical instrument, and a storage device. The robotic surgical system includes a robot arm including at least one operable interface configured to provide an input, at least one motor, and a control device configured to control the at least one motor to provide the input to the at least one operable interface. The surgical instrument includes at least one input coupler configured to operably couple with the at least one operable interface to receive the input therefrom, an end effector assembly, and an actuation assembly operably coupled between the at least one input coupler and the end effector assembly such that, in response receipt of the input by the at least one input coupler, the end effector assembly is manipulated. The storage device stores setting information and adjustment information. The control device is configured to access the setting information and the adjustment information and determine whether to utilize the setting information to control the at least one motor to provide a first input to the at least one operable interface to achieve a desired manipulation of the end effector assembly or to adjust the setting information based on the adjustment information to control the at least one motor to provide a second, different input to the at least one operable interface to achieve the desired manipulation of the end effector assembly.

In an aspect of the present disclosure, determining whether to provide the first input or the second input includes considering additional information including use information and/or condition information.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
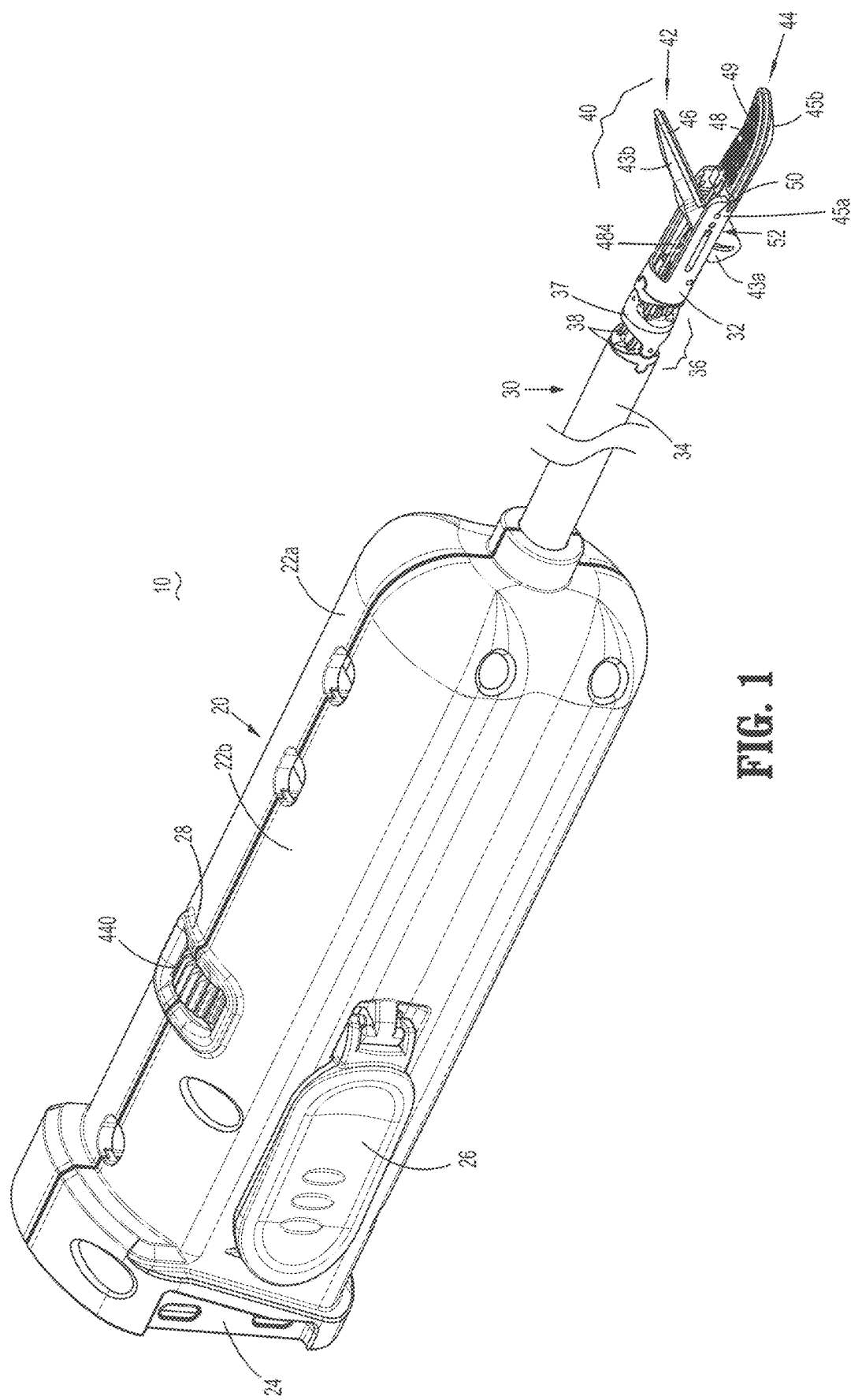
FIG. 1 is a perspective view of a surgical instrument provided in accordance with the present disclosure configured for mounting on a robotic arm of a robotic surgical system.
Figure 2A:
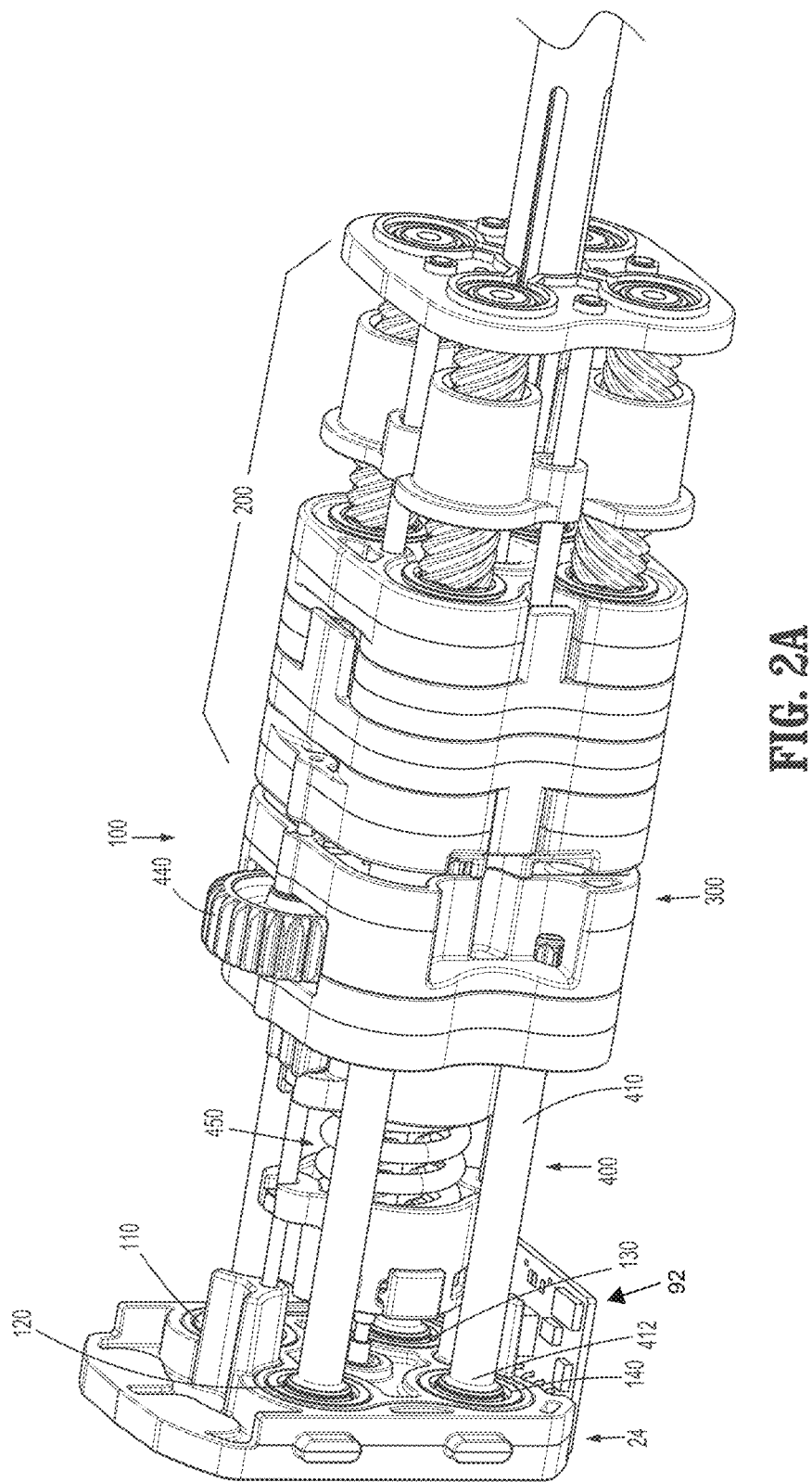
FIG. 2A is a front, perspective view of a proximal portion of the surgical instrument of FIG. 1 with an outer shell removed.
Figure 2B:
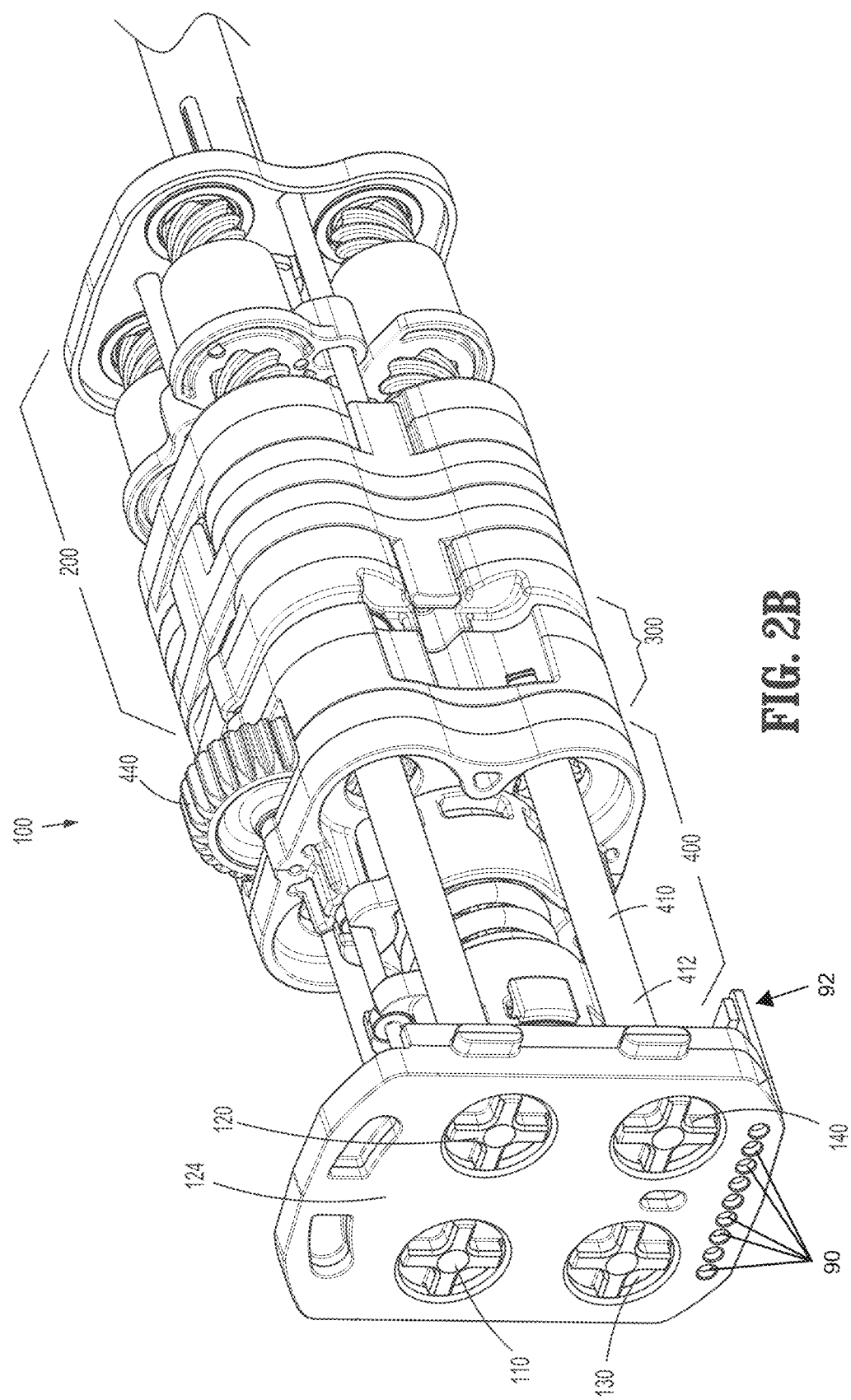
FIG. 2B is a rear, perspective view of the proximal portion of the surgical instrument of FIG. 1 with the outer shell removed.
Figure 3:
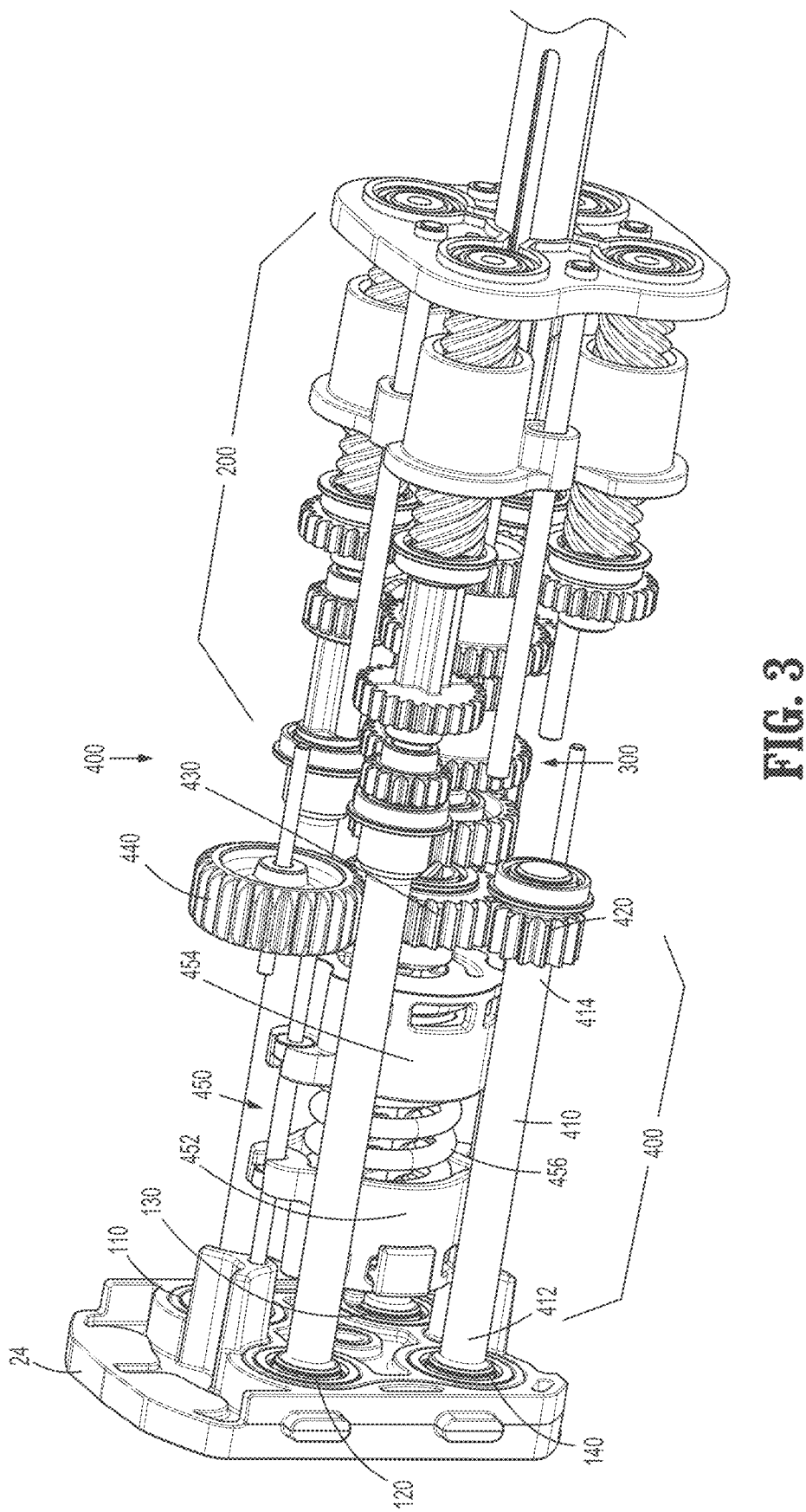
FIG. 3 is a front, perspective view of the proximal portion of the surgical instrument of FIG. 1 with the outer shell and additional internal components removed.
Figure 4:
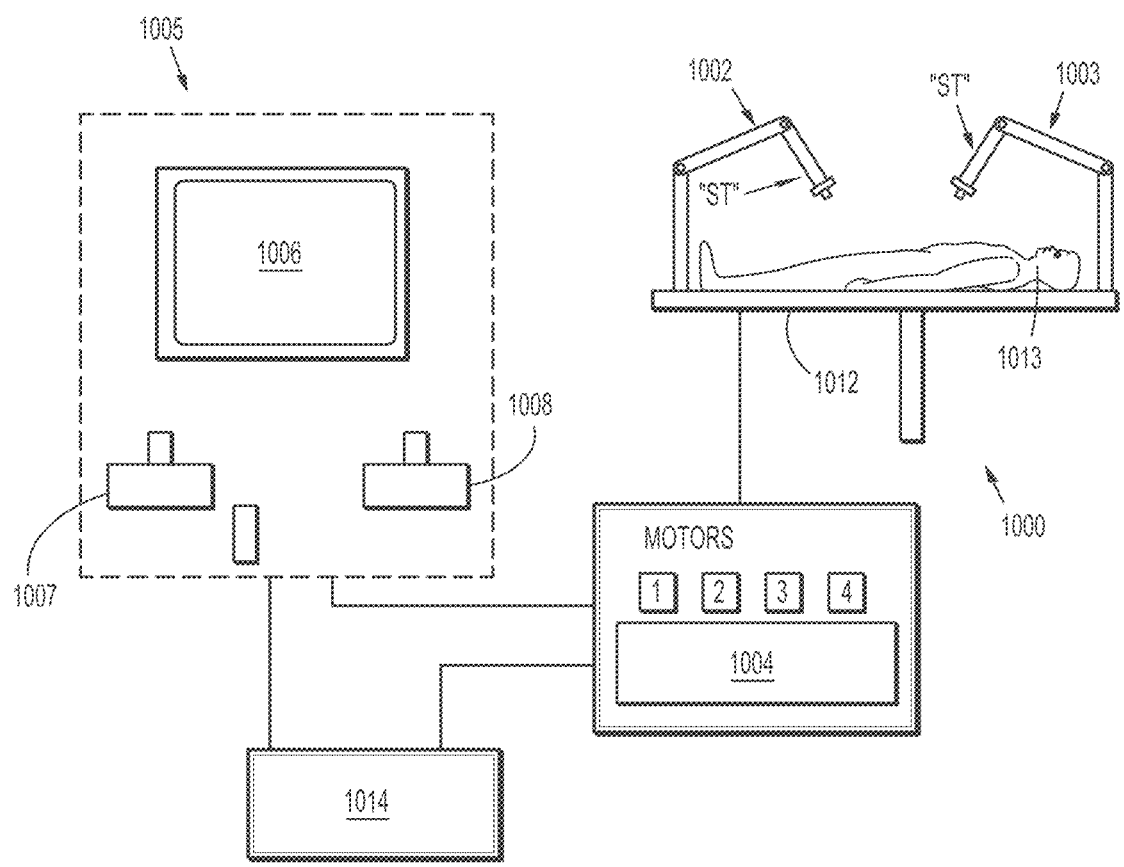
FIG. 4 is a schematic illustration of an exemplary robotic surgical system configured to releasably receive the surgical instrument of FIG. 1.

Referring to FIGS. 1-3, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with end effector assembly 40. Instrument 10 is detailed herein as an articulating electrosurgical forceps configured for use with a robotic surgical system, e.g., robotic surgical system 1000 (FIG. 4). However, the aspects and features of instrument 10 provided in accordance with the present disclosure, detailed below, are equally applicable for use with other suitable surgical instruments, e.g., graspers, staplers, clip appliers, and/or in other suitable surgical systems, e.g., motorized or other power-driven systems.

With particular reference to FIG. 1, housing 20 of instrument 10 includes first and second body portion 22a, 22b and a proximal face plate 24 that cooperate to enclose actuation assembly 100 therein. Proximal face plate 24 includes apertures defined therein through which input couplers 110-140 (FIG. 2B) of actuation assembly 100 extend. A pair of latch levers 26 (only one of which is illustrated in FIG. 1) extending outwardly from opposing sides of housing 20 enable releasable engagement of housing 20 with a robotic arm of a surgical system, e.g., robotic surgical system 1000 (FIG. 4). An aperture 28 defined through housing 20 permits thumbwheel 440 to extend therethrough to enable manual manipulation of thumbwheel 440 from the exterior of housing 20 to permit manual opening and closing of end effector assembly 40.

Referring also to FIGS. 2A-3, a plurality of electrical contacts 90 extend through one or more apertures defined through proximal face plate 24 to enable electrical communication between instrument 10 and robotic surgical system 1000 (FIG. 4) when instrument 10 is engaged thereon, e.g., for the communication of data, control, and/or power signals therebetween. As an alternative to electrical contacts 90 extending through proximal face plate 24, other suitable transmitter, receiver, and/or transceiver components to enable the communication of data, control, and/or power signals are also contemplated, e.g., using RFID, Bluetooth®, WiFi®, or via any other suitable wired, wireless, contacted, or contactless communication method. At least some of the electrical contacts 90 are electrically coupled with electronics 92 mounted on an interior side of proximal face plate 24, e.g., within housing 20. Electronics 92 may include, for example, a storage device, a communications device (including suitable input/output components), and a CPU including a memory and a processor. Electronics 92 may be mounted on a circuit board or otherwise configured, e.g., as a chip.

The storage device of electronics 92 stores information relating to surgical instrument such as, for example: the item number, e.g., SKU number; date of manufacture; manufacture location, e.g., location code; serial number; lot number; use information; setting information; adjustment information; calibration information; security information, e.g., encryption key(s), and/or other suitable additional or alternative data. The storage device of electronics 92 may be, for example, a magnetic disk, flash memory, optical disk, or other suitable data storage device.

As an alternative or in addition to storing the above-noted information in the storage device of electronics 92, some or all of such information, e.g., the use information, calibration information, setting information, and/or adjustment information, may be stored in a storage device associated with robotic surgical system 1000 (FIG. 4), a remote server, a cloud server, etc., and accessible via instrument 10 and/or robotic surgical system 1000 (FIG. 4). In such configurations, the information may, for example, be updated by manufacturer-provided updates, and/or may be applied to individual instruments, units of instruments (e.g., units from the same manufacturing location, manufacturing period, lot number, etc.), or across all instruments. Further still, even where the information is stored locally on each instrument, this information may be updated by manufacturer-provided updates manually or automatically upon connection to the robotic surgical system 1000 (FIG. 4).

Referring again to FIG. 1, shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extend through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation sub-assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated. In some configurations, as an alternative, shaft 30 is substantially rigid, malleable, or flexible and not configured for active articulation.

With respect to articulation of end effector assembly 40 relative to proximal segment 34 of shaft 30, actuation of articulation cables 38 may be accomplished in pairs. More specifically, in order to pitch end effector assembly 40, the upper pair of cables 38 are actuated in a similar manner while the lower pair of cables 38 are actuated in a similar manner relative to one another but an opposite manner relative to the upper pair of cables 38. With respect to yaw articulation, the right pair of cables 38 are actuated in a similar manner while the left pair of cables 38 are actuated in a similar manner relative to one another but an opposite manner relative to the right pair of cables 38. Other configurations of articulation cables 38 or other articulation actuators are also contemplated.

Continuing with reference to FIG. 1, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g., a closed position of end effector assembly 40) for grasping tissue "T" (FIGS. 8 and 10) between tissue-contacting surfaces 46, 48. As an alternative to this unilateral configuration, a bilateral configuration may be provided whereby both jaw members 42, 44 are pivotable relative to one another and distal segment 32 of shaft 30. Other suitable jaw actuation mechanisms are also contemplated.

In configurations, a longitudinally-extending knife channel 49 (only knife channel 49 of jaw member 44 is illustrated; the knife channel of jaw member 42 is similarly configured) is defined through the tissue-contacting surface 46, 48 of one or both jaw members 42, 44. In such embodiments, a knife assembly including a knife tube (not shown) extending from housing 20 through shaft 30 to end effector assembly 40 and a knife blade (not shown) disposed within end effector assembly 40 between jaw members 42, 44 is provided. The knife blade is selectively translatable through the knife channel(s) 49 and between the jaw member 42, 44 to cut tissue "T" (FIGS. 8 and 10) grasped between tissue-contacting surfaces 46, 48 of jaw members 42, 44, respectively. The knife tube is operably coupled to a knife drive sub-assembly 300 (FIG. 3) of actuation assembly 100 (FIGS. 2A-2B) at a proximal end thereof to enable the selective actuation of the knife tube to, in turn, reciprocate the knife blade (not shown) between jaw members 42, 44 to cut tissue "T" (FIGS. 8 and 10) grasped between tissue-contacting surfaces 46, 48. As an alternative to a longitudinally-advanceable mechanical knife, other suitable mechanical cutters are also contemplated, e.g., guillotine-style cutters, as are energy-based cutters, e.g., RF electrical cutters, ultrasonic cutters, etc., in static or dynamic configurations.

Referring still to FIG. 1, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive sub-assembly 400 of actuation assembly 100 (FIGS. 2A-2B) to enable selective actuation of end effector assembly 40 to grasp tissue "T" (FIGS. 8 and 10) therebetween and apply a jaw force within an appropriate jaw force range, as detailed below.

Tissue-contacting surfaces 46, 48 of jaw members 42, 44, respectively, are at least partially formed from an electrically conductive material and are energizable to different potentials to enable the conduction of RF electrical energy through tissue "T" (FIGS. 8 and 10) grasped therebetween, although tissue-contacting surfaces 46, 48 may alternatively be configured to supply any suitable energy, e.g., thermal, microwave, light, ultrasonic, ultrasound, etc., through tissue "T" (FIGS. 8 and 10) grasped therebetween for energy-based tissue treatment. Instrument 10 defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue "T" (FIGS. 8 and 10) grasped between tissue-contacting surfaces 46, 48.

With additional reference to FIGS. 2A-3, as noted above, actuation assembly 100 is disposed within housing 20 and includes an articulation sub-assembly 200, a knife drive sub-assembly 300, and a jaw drive sub-assembly 400. Articulation sub-assembly 200 is operably coupled between first and second input couplers 110, 120, respectively, of actuation assembly 100 and articulation cables 38 (FIG. 1) such that, upon receipt of appropriate inputs into first and/or second input couplers 110, 120, articulation sub-assembly 200 manipulates cables 38 (FIG. 1) to articulate end effector assembly 40 in a desired direction, e.g., to pitch and/or yaw end effector assembly 40.

Knife drive sub-assembly 300 is operably coupled between third input coupler 130 of actuation assembly 100 and the knife tube such that, upon receipt of appropriate input into third input coupler 130, knife drive sub-assembly 300 manipulates the knife tube to reciprocate the knife blade between jaw members 42, 44 to cut tissue "T" (FIGS. 8 and 10) grasped between tissue-contacting surfaces 46, 48.

Jaw drive sub-assembly 400, as detailed below, is operably coupled between fourth input coupler 140 of actuation assembly 100 and drive rod 484 such that, upon receipt of appropriate input into fourth input coupler 140, jaw drive sub-assembly 400 pivots jaw members 42, 44 between the spaced-apart and approximated positions to grasp tissue "T" (FIGS. 8 and 10) therebetween and apply a jaw force within an appropriate jaw force range.

Actuation assembly 100 is configured to operably interface with a robotic surgical system 1000 (FIG. 4) when instrument 10 is mounted on robotic surgical system 1000 (FIG. 4), to enable robotic operation of actuation assembly 100 to provide the above-detailed functionality. That is, robotic surgical system 1000 (FIG. 4) selectively provides inputs, e.g., rotational inputs to input couplers 110-140 of actuation assembly 100 to articulate end effector assembly 40, grasp tissue "T" (FIGS. 8 and 10) between jaw members 42, 44, and/or cut tissue "T" (FIGS. 8 and 10) grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 1000 (FIG. 4) is generally described.

Turning to FIG. 4, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and a mounted device which may be, for example, a surgical tool "ST." One or more of the surgical tools "ST" may be instrument 10 (FIG. 1), thus providing such functionality on a robotic surgical system 1000.

Robot arms 1002, 1003 may be driven by electric drives, e.g., motors, connected to control device 1004. The motors, for example, may be rotational drive motors configured to provide rotational inputs, e.g., to selectively rotationally drive input couplers 110-140 (FIG. 2B) of surgical instrument (FIG. 1) to accomplish a desired task or tasks. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Control device 1004, more specifically, may control one or more of the motors based on rotation, e.g., controlling to rotational position using a rotational position encoder (or Hall effect sensors or other suitable rotational position detectors) associated with the motor to determine a degree of rotation output from the motor and, thus, the degree of rotational input provided to the corresponding input coupler 110-140 (FIG. 2B) of surgical instrument 10 (FIG. 1). Alternatively or additionally, control device 1004 may control one or more of the motors based on torque, current, or in any other suitable manner.

Figure 5:
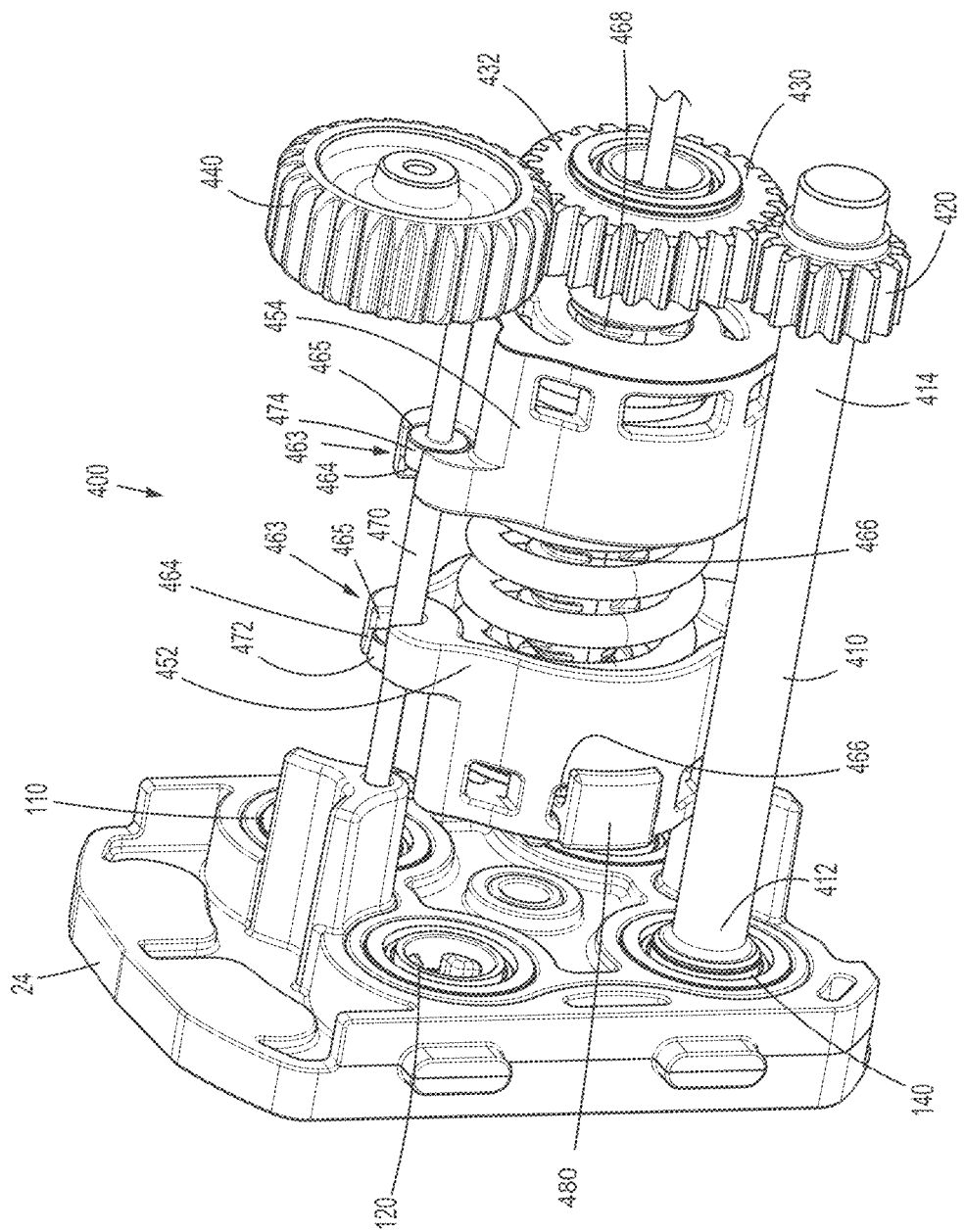
FIG. 5 is a front, perspective view of a jaw drive sub-assembly of the surgical instrument of FIG. 1.
Figure 6:
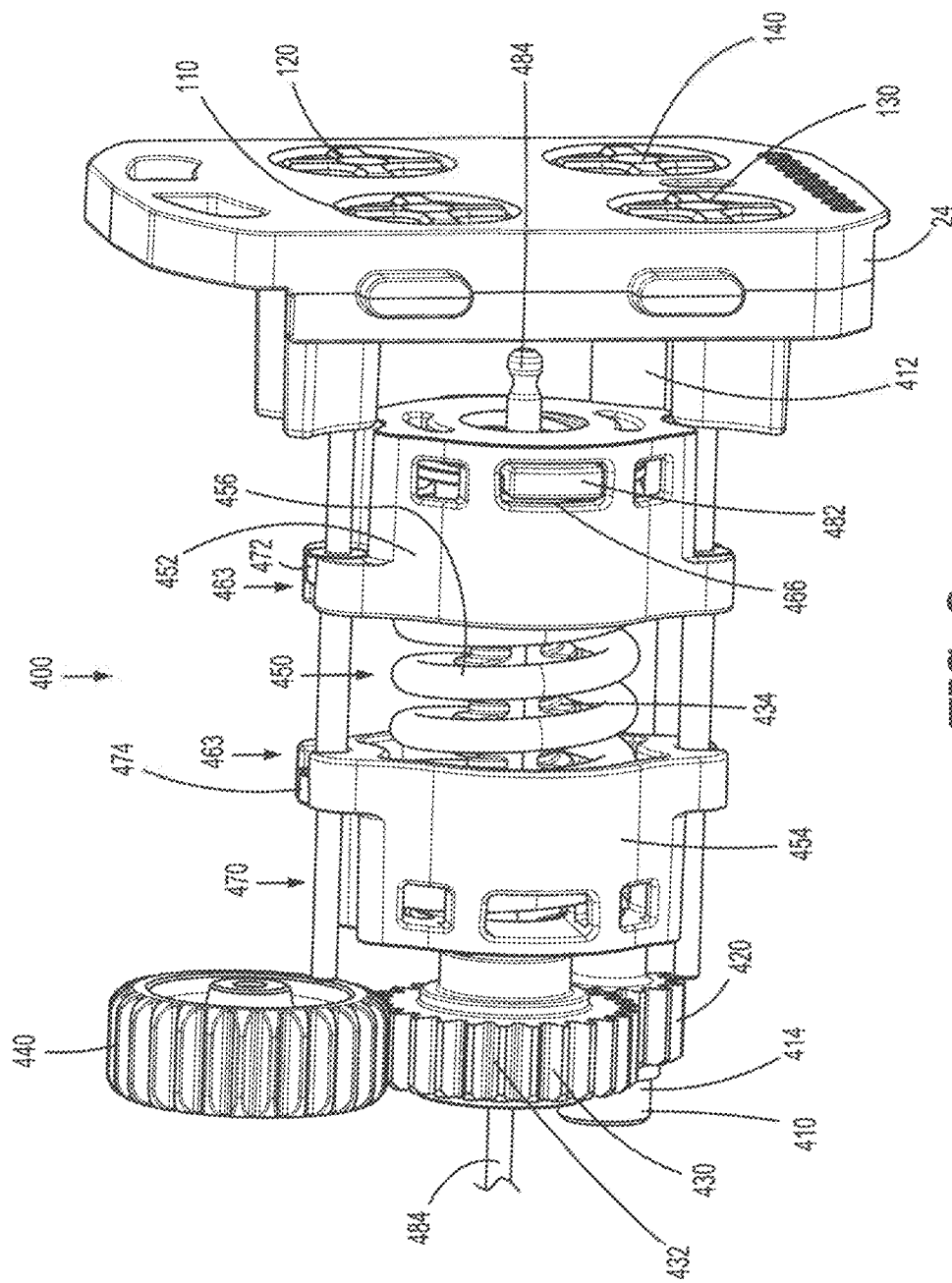
FIG. 6 is a rear, perspective view of the jaw drive sub-assembly of the surgical instrument of FIG. 1.
Figure 7:
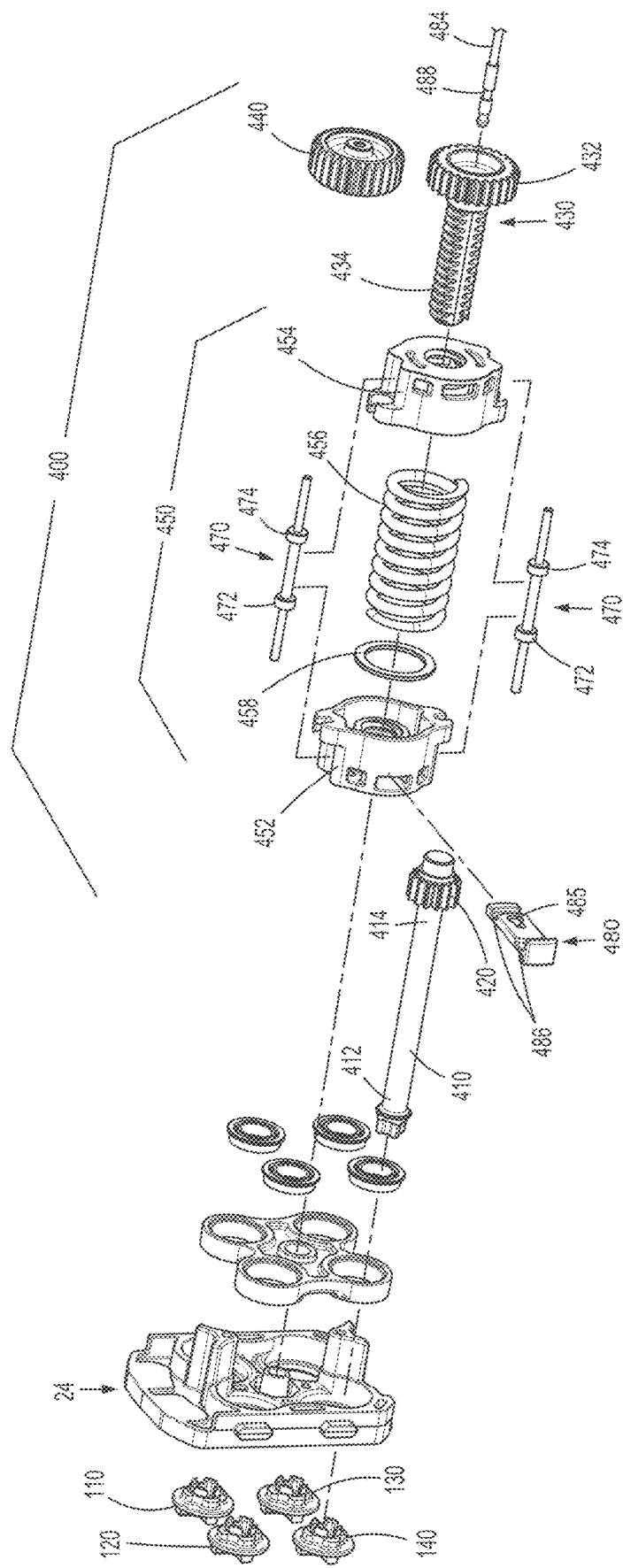
FIG. 7 is an exploded, perspective view of the jaw drive sub-assembly of the surgical instrument of FIG. 1.

With reference to FIG. 5-7, jaw drive sub-assembly 400 of actuation assembly 100 is shown generally including an input shaft 410, an input gear 420, a drive gear 430, a thumbwheel 440, a spring force assembly 450, and a drive rod assembly 480.

Input shaft 410 includes a proximal end portion 412 operably coupled to fourth input coupler 140 and a distal end portion 414 having input gear 420 engaged thereon such that rotational input provided to fourth input coupler 140 drives rotation of input shaft 410 to, thereby, drive rotation of input gear 420. Input gear 420 is disposed in meshed engagement with round gear 432 of drive gear 430 such that rotation of input gear 420, e.g., in response to a rotational input provided at fourth input coupler 140, effects rotation of drive gear 430 in an opposite direction. Thumbwheel 440 is also disposed in meshed engagement with round gear 432 of drive gear 430 such that rotation of thumbwheel 440 effects rotation of drive gear 430 in an opposite direction, thus enabling manual driving of drive gear 430 via manipulation of thumbwheel 440. Drive gear 430, in addition to round gear 432, further includes a lead screw 434 fixedly engaged, e.g., monolithically formed, with round gear 432 such that rotation of round gear 432 effects similar rotation of lead screw 434.

Spring force assembly 450 includes a proximal hub 452, a distal hub 454, a compression spring 456, and a spring washer 458, although suitable force-limiting assemblies are also contemplated such as, for example, utilizing a torsion spring, a compliant feature, etc. Spring force assembly 450 further includes a pair of guide bars 470.

Proximal and distal hubs 452, 454 of spring force assembly 450 may be identical components that are oriented, positioned, and/or coupled to other components differently, thus providing different functionality while reducing the number of different parts required to be manufactured. The features of proximal and distal hubs 452, 454 are detailed below to the extent necessary to facilitate understanding of the present disclosure and, thus, although some features may be detailed with respect to only one of the proximal or distal hub 452, 454 and the function associated therewith, similar features may be provided on the other of the proximal or distal hub 452, 454 without the associated function. Alternatively, proximal and distal hubs 452, 454 may be manufactured as different components.

Proximal and distal hubs 452, 454 of spring force assembly 450 each include a retainer guide 463 extending radially outwardly from opposed sides thereof. Each retainer guide 463 defines a trough 464 and includes a shoulder 465 extending into the respective trough 464. Proximal and distal hubs 452, 454 are oppositely-oriented relative to one another such that the open ends of the cavities defined therein face one another and such that the shoulder 465 of each pair of retainer guides 463 of proximal and distal hubs 452, 454 face away from one another.

Figure 9:
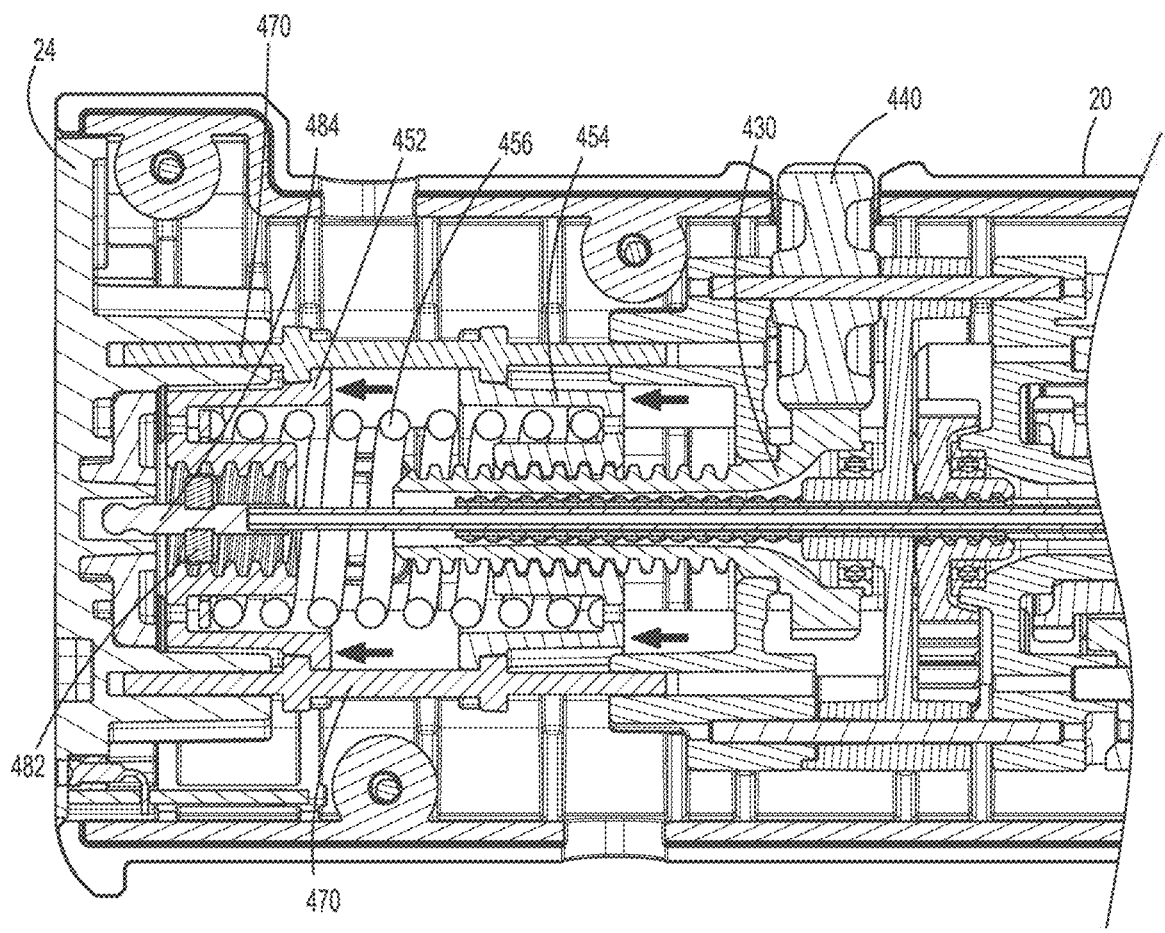
FIG. 9 is a longitudinal, cross-sectional view of a proximal portion of the surgical instrument of FIG. 1 illustrating the jaw drive sub-assembly transitioning the end effector assembly from the open position towards a closed position.
Figure 11:
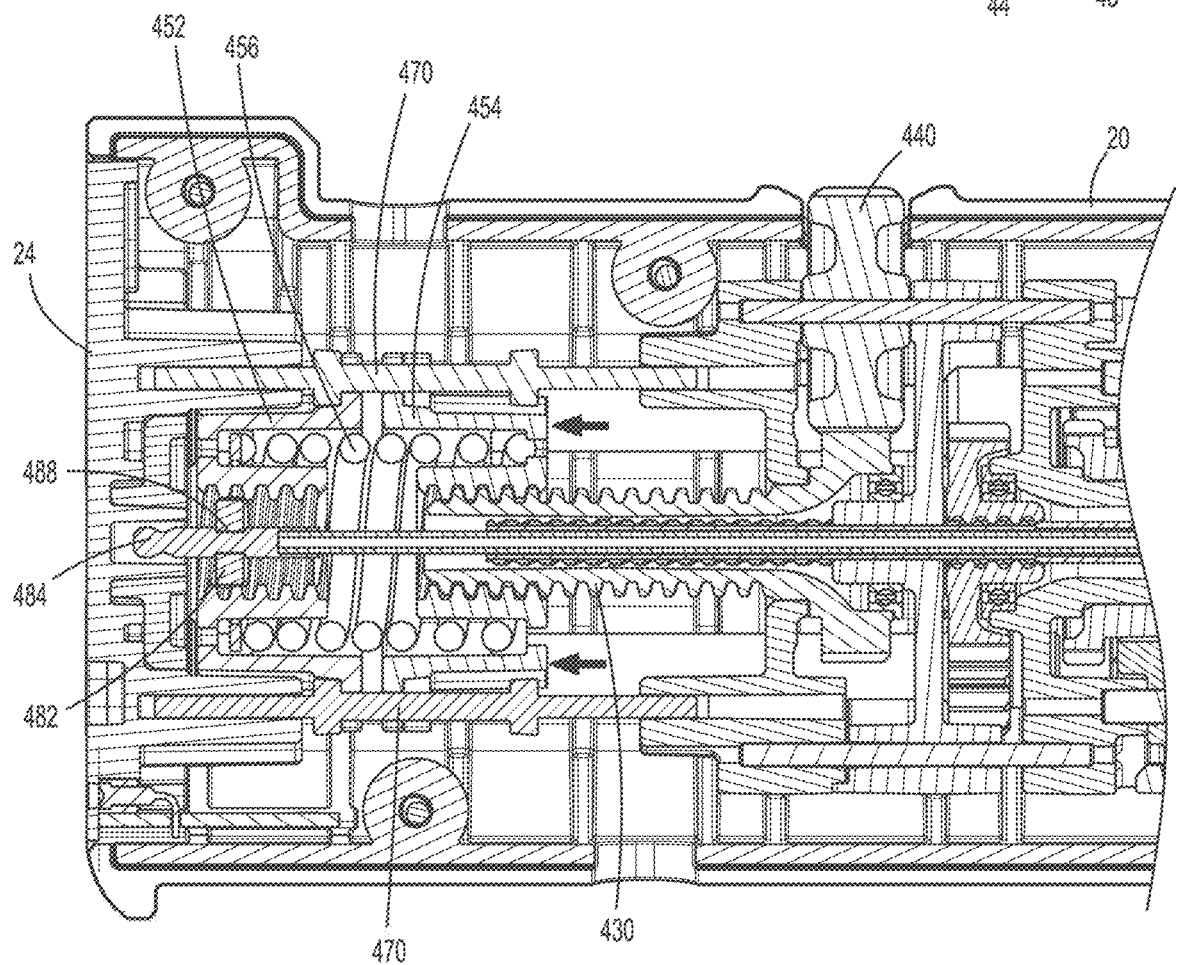
FIG. 11 is a longitudinal, cross-sectional view of the proximal portion of the surgical instrument of FIG. 1 illustrating the jaw drive sub-assembly retaining the end effector assembly in the closed position.

Proximal hub 452 further includes a transverse slot 466 defined therethrough that is configured to receive lock plate 482 of drive rod assembly 480 to fix lock plate 482 and, thus, a proximal end portion of drive rod 484 relative to proximal hub 452 (see FIGS. 9 and 11). Once engaged in this manner, drive rod 484 is locked in position coaxially disposed through proximal hub 452, distal hub 454, compression spring 456, and drive gear 430.

Distal hub 454 defines a threaded central bore 468 extending therethrough. Threaded central bore 468 receives lead screw 434 of drive gear 430 therethrough in threaded engagement therewith such that rotation of lead screw 434 drives translation of distal hub 454 longitudinally along lead screw 434.

Compression spring 456 is disposed between proximal and distal hubs 452, 454 with a proximal portion thereof disposed within the cavity defined within proximal hub 452 and a distal portion thereof disposed within the cavity defined within distal hub 462. At least a portion of compression spring 456 is disposed about and/or configured to receive a portion of lead screw 434 of drive gear 430 therethrough. Spring washer 458 is positioned within the cavity of proximal hub 452 between proximal hub 452 and compression spring 456, although other configurations are also contemplated.

Each guide bar 470 is slidably received within the troughs 464 of the corresponding pair of retainer guides 463 of proximal and distal hubs 452, 454. Each guide bar 470 includes a pair of spaced-apart rims 472, 474 engaged thereon that are configured to abut shoulders 465 of the respective retainer guides 463, thereby defining a maximum distance between proximal and distal hubs 452, 454. However, proximal and/or distal hubs 452, 454 are permitted to slide along guide bars 470 towards one another, as detailed below.

Continuing with reference to FIGS. 5-7, drive rod assembly 480 includes lock plate 482 and drive rod 484. Lock plate 482 defines a central keyhole 485 and a pair of slots 486, e.g., arcuate slots, defined on a distal face of lock plate 482 on either side of central keyhole 485. Lock plate 482 is configured for insertion through transverse slot 466 of proximal hub 452 and, once installed therein, portions of spring washer 458 are configured for receipt within slots 486 to secure lock plate 482 in engagement within proximal hub 452. Spring washer 458 is maintained in position within slots 486 under the bias of compression spring 456 which, at the maximum distance between proximal and distal hubs 452, 454 (as set by rims 472, 474 of guide bars 470 and shoulders 465 of retainer guides 463), is pre-compressed.

Drive rod 484, as noted above, includes a distal end portion operably coupled to cam-slot assembly 52 of end effector assembly 40 (FIG. 1). Drive rod 484 extends proximally through shaft 30, housing 20, and actuation assembly 100 (see FIGS. 1-3) and is engaged within lock plate 482 at a proximal end portion of drive rod 484. More specifically, drive rod 484 defines a waist 488 towards the proximal end thereof that is configured to lock in engagement within central keyhole 485 of lock plate 482, e.g., via longitudinal translation of drive rod 484 into central keyhole 485 until waist 488 is aligned with central keyhole 485, followed by transverse movement of drive rod 484 relative to lock plate 482, to thereby fix the proximal end portion of drive rod 484 relative to lock plate 482 and, thus, relative to proximal hub 452 due to the engagement of lock plate 482 within proximal hub 452.

Referring to FIGS. 8-11, in use, jaw members 42, 44 are initially disposed in the spaced-apart position (FIG. 8) and, correspondingly, proximal and distal hubs 452, 454 are disposed in a distal-most position such drive rod 484 is disposed in a distal-most position (FIG. 9). Further, in this position, compression spring 456 is disposed in a least-compressed condition; although, as noted above, even in the least-compressed condition, compression spring 456 is partially compressed due to the retention of compression spring 456 in a pre-compressed configuration between proximal and distal hubs 452, 454.

Figure 8:
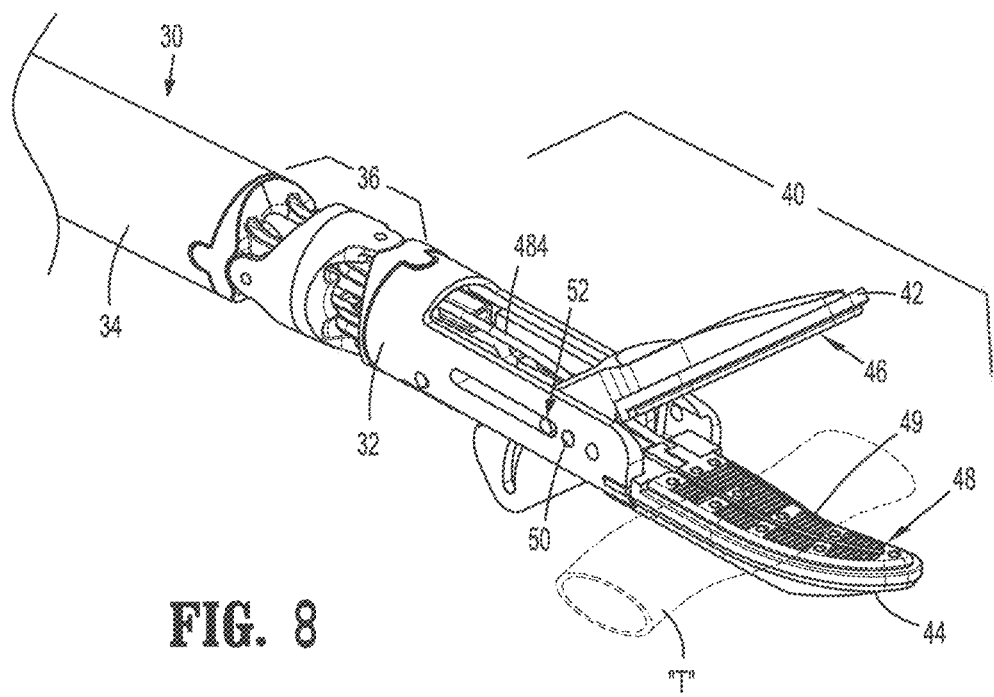
FIG. 8 is a perspective view of a distal portion of the surgical instrument of FIG. 1 with the end effector assembly disposed in an open position.
Figure 10:
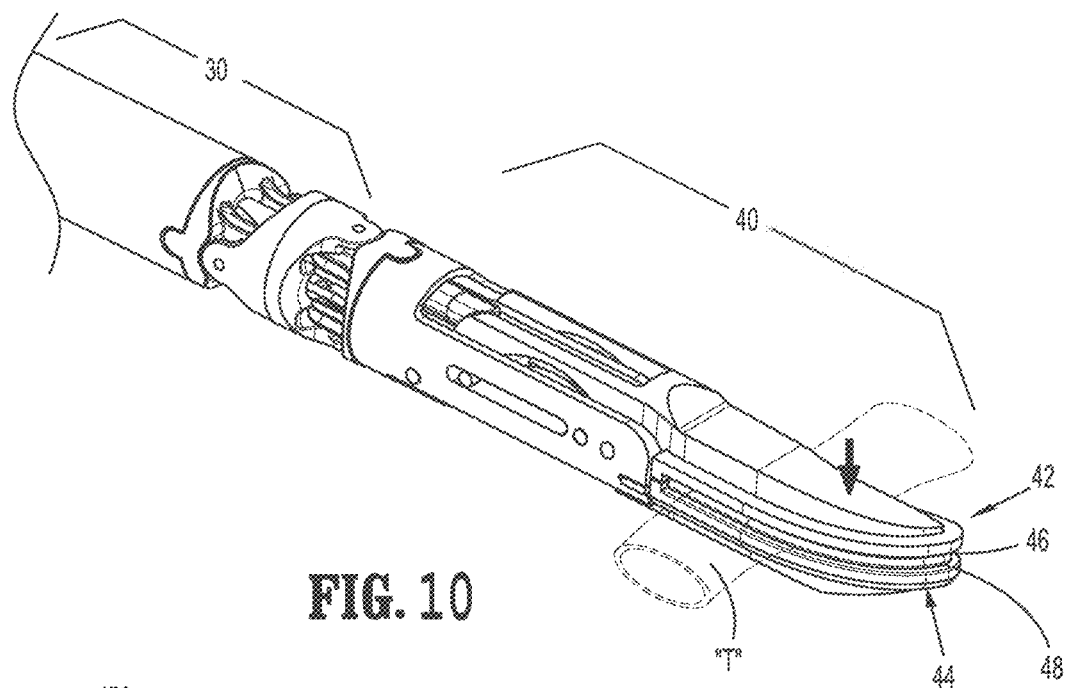
FIG. 10 is a perspective view of the distal portion of the surgical instrument of FIG. 1 with the end effector assembly disposed in the closed position.

In response to an input to close end effector assembly 40, e.g., rotational input by the corresponding motor of robotic surgical system 1000 (FIG. 4) to fourth input coupler 140 (FIGS. 5-7), drive shaft 410 is rotated to thereby rotate input gear 420 which, in turn, rotates drive gear 430 such that distal hub 454 is translated proximally towards proximal hub 452 (see FIG. 9). Proximal translation of distal hub 454 urges distal hub 454 against compression spring 456. Initially, where forces resisting approximation of jaw members 42, 44 are below a threshold corresponding to the spring value of compression spring 456, the jaw force applied by jaw members 42, 44 is relatively low such that the urging of distal hub 454 proximally against compression spring 456 urges compression spring 456 proximally which, in turn, urges lock plate 482 and, thus, drive rod 484 proximally to pivot jaw member 42 relative to jaw member 44 from the spaced-apart position towards the approximated position to grasp tissue "T" therebetween (FIGS. 8 and 10).

Upon further approximation of jaw members 42, 44 to grasp tissue "T" therebetween, the forces resisting approximation of jaw members 42, 44, e.g., tissue "T" resisting compression, may reach the threshold and, thus the jaw force applied by jaw members 42, 44 may reach a corresponding threshold. In order to maintain the jaw force applied by jaw members 42, 44 within a jaw force range such as, for example, from about 3 kg/cm$^2$ to about 16 kg/cm$^2$, application of further jaw force by jaw members 42, 44 is inhibited beyond the threshold point despite further rotational input to fourth input coupler 140 (FIGS. 5-7). More specifically, once the threshold has been reached, further rotational input to fourth input coupler 140 (FIGS. 5-7) rotates drive shaft 410, input gear 420, and drive gear 430 to translate distal hub 454 further proximally into compression spring 456. However, rather than compression spring 456 urging proximal hub 452 further proximally to continue approximation of jaw members 42, 44 and increase the closure force applied therebetween, compression spring 456 is compressed, enabling proximal hub 452 and, thus, drive rod 484 to remain in position, thus inhibiting application of additional jaw force between jaw members 42, 44 (see FIGS. 10 and 11).

With tissue "T" grasped between jaw members 42, 44 under an appropriate jaw force, energy may be supplied to jaw members 42, 44 to treat, e.g., seal tissue "T." Thereafter, the knife blade (not shown) may be advanced between jaw members 42, 44 to cut the treated tissue "T," e.g., by providing a rotational input to input coupler 130 (FIG. 6) to actuate knife drive sub-assembly 300 to translate the knife tube distally to thereby advance the knife blade (not shown) between jaw members 42, 44 to cut the treated tissue "T." Alternatively, tissue "T" may be cut without first treating the tissue "T" and/or tissue "T" may be treated without subsequent cutting.

Once tissue "T" is cut, an opposite rotation input is provided to input coupler 130 (FIG. 6) to return the knife blade (not shown) to its initial position proximally of body portions 43b, 45b of jaw members 42, 44 (see FIG. 1). Thereafter, an opposite input is provided to input coupler 140 (FIGS. 5-7) to return jaw members 42, 44 back towards the spaced-apart position to release the sealed and/or cut tissue.

Referring generally to FIGS. 1-11, as detailed above, calibration information, setting information, use information, and adjustment information, among other information, are stored in the storage device of electronics 92 of instrument 10, in robotic surgical system 1000 (FIG. 4), and/or in other accessible storage devices. The calibration information may include an algorithm(s), set point(s), look-up table(s), machine learning program(s), and/or other information to enable determination of home/initial positions of the various components of instrument 10 such as, for example: the open position of jaw members 42, 44, the retracted position of the knife blade, the un-articulated configuration of shaft 30 and end effector assembly 40, etc.

The setting information may include, for example, jaw drive information, e.g., a degree of rotational input to input coupler 140 required to move jaw members 42, 44 from the open position towards the closed position to grasp tissue "T" between tissue-contacting surfaces 46, 48 and apply a jaw force or jaw force within a jaw force range thereto; knife deployment information, e.g., a degree of rotational input to input coupler 130 required to deploy the knife blade from the retracted position to an extended position to cut tissue "T" between tissue-contacting surfaces 46, 48; and/or articulation control information, e.g., a degree of rotational input to input couplers 110 and/or 120 required to articulate end effector assembly 40 from the un-articulated position to one or more articulated positions (for example, a maximum positive yaw position, a maximum negative yaw position, a maximum positive pitch position, and a maximum negative pitch position); etc. The setting information may be determined based on testing during manufacturing (e.g., for each instrument, each unit of instruments, or for all instruments), may be determined via mathematical simulation, utilizing machine learning, using theoretical formulae, combinations thereof, etc.

The use information may include, for example, a number of connections to a robotic surgical system, elapsed time of use/connection, elapsed idle time, elapsed time of active use, age (time since manufacture), number of jaw member approximations, number of energy activations, number and/or manner of articulations, number of knife blade deployments, etc. Robotic surgical system 1000 may write and/or update the use information stored in the storage device 92 of instrument 10 (and/or elsewhere) periodically, continuously, upon occurrence of an event, or in any other suitable manner.

Some or all of the setting information may be basis information that can be adjusted periodically, continuously, upon occurrence of certain events, and/or based on external inputs (user-provided input, sensor or other component feedback, etc.). For example, the basis setting information may be adjusted, e.g., at robotic surgical system 1000, based upon one or more current conditions of the instrument 10 and/or the current use information, as indicated by the adjustment information. The adjustment information for each corresponding setting may include an algorithm(s), set point(s), look-up table(s), machine learning program(s), etc. The adjustment information may be determined experimentally, via mathematical simulation, utilizing machine learning, using theoretical formulae, combinations thereof, etc.

By way of example, the jaw drive setting information may provide basis information indicating that "X" degrees of rotational input to input coupler 140 is required to move jaw members 42, 44 from the open position towards the closed position to grasp tissue "T" between tissue-contacting surfaces 46, 48 and apply a jaw force or jaw force within a jaw force range thereto. Thus, in the absence of modification to this jaw drive setting information, upon receiving a signal to approximate jaw members 42, 44 to grasp tissue between tissue-contacting surfaces 46, 48 for tissue treatment, e.g., sealing, control device 1004 controls the appropriate motor(s) of robotic surgical system 1000 to impart "X" degrees of rotational input to input coupler 140 such that tissue-contacting surfaces 46, 48 grasp tissue "T" therebetween under the applied jaw force or jaw force within the jaw force range.

However, it has been found that the jaw force or jaw force range applied in response to input of a set degree of rotational input to input coupler 140 may vary over the usable life of instrument 10 and/or based upon a current condition of instrument 10, e.g., whether end effector assembly 40 is disposed in an un-articulated position, partially articulated position, or fully articulated position. The stage of useable life of instrument 10 may be determined based upon some or all of the above-noted use information and may affect the jaw force or jaw force range due to, for example, changes in component stiffness/elasticity, establishment of "memory" positions of components/connections, changes in force transmission across joints/connections, changes in tolerances, changes in frictional loss, component wear, component and/or joint/connection degradation, etc. The current condition of instrument 10 may be determined by control device 1004 and/or other components of robotic surgical system 1000 based upon feedback data, previous inputs, visual or other tracking information, etc., and may affect the jaw force or jaw force range due to actuation force changes, actuation distance changes, friction changes, etc.

In order to account for the above changes, the adjustment information enables adjustment of the basis jaw drive setting, e.g., "X" degrees, to an adjusted jaw drive setting, e.g., "Y" degrees, based upon the use and/or current condition of instrument 10 using the algorithm(s), set point(s), look-up table(s), machine learning program(s), etc. As such, with the adjusted jaw drive setting information implemented, upon receiving a signal to approximate jaw members 42, 44 to grasp tissue between tissue-contacting surfaces 46, 48 for tissue treatment, e.g., sealing, control device 1004 controls the appropriate motor(s) of robotic surgical system 1000 to impart "Y" degrees of rotational input to input coupler 140 such that tissue-contacting surfaces 46, 48 grasp tissue "T" therebetween under the applied jaw force or jaw force within the jaw force range. Thus, the same jaw force or jaw force range is achieved despite changing input requirements.

The present disclosure, however, is not limited to adjusting jaw drive setting information for applying jaw force but, rather, may apply to adjustment of any other suitable setting information, e.g., knife deployment information, articulation control information, etc. Further, the present disclose is not limited to instrument 10 but may also apply to any other suitable surgical instrument. Indeed, the methods provided in accordance with the present disclosure and detailed below with reference to FIGS. 12 and 13 may be utilized with instrument 10 for adjusting jaw drive setting information or may be utilized with any other suitable instrument and/or desired manipulation thereof.

Figure 12:
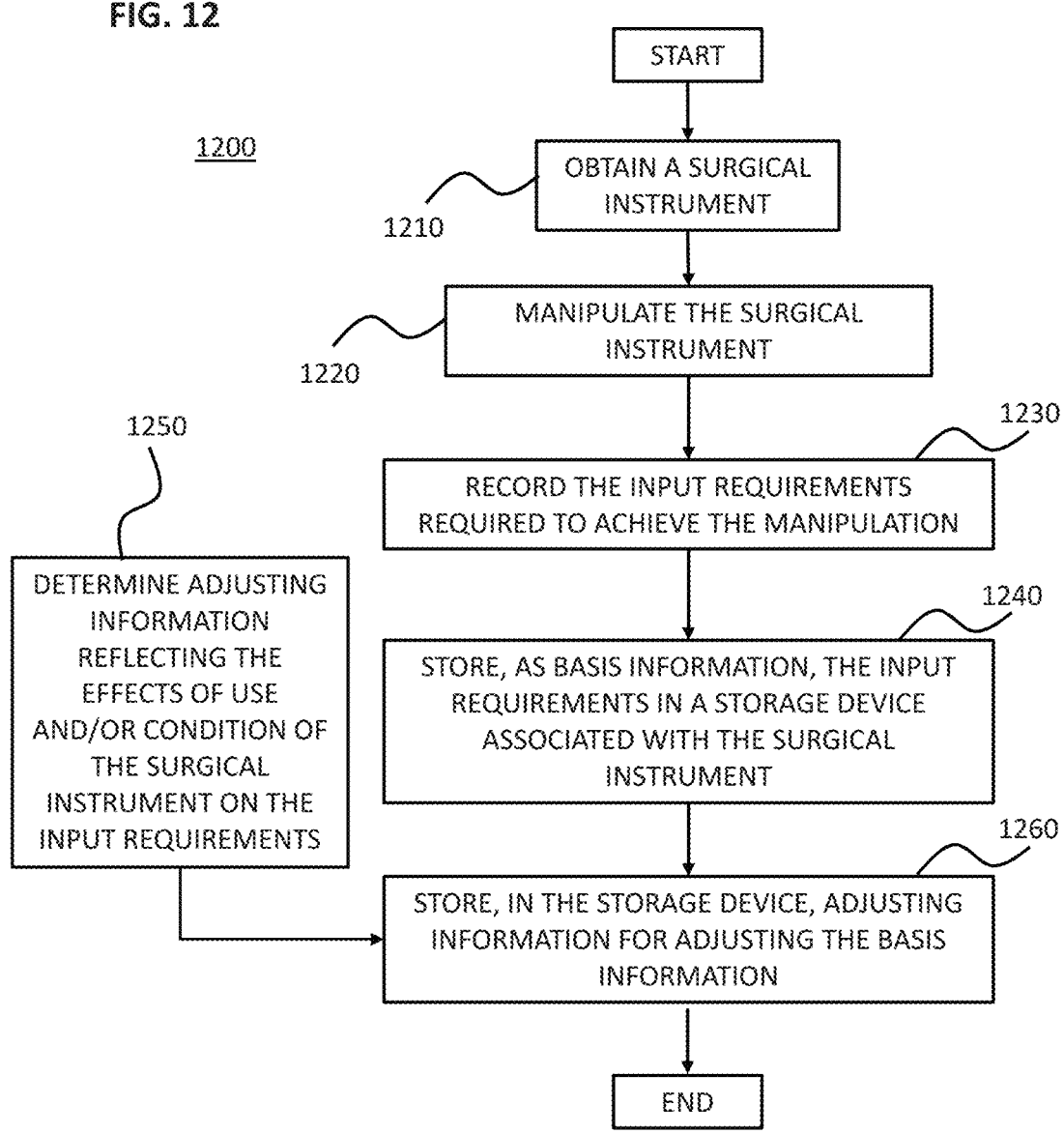
FIGS. 12 and 13 are flow diagrams illustrating methods provided in accordance with the present disclosure.

Turning to FIG. 12, a testing and/or manufacturing method 1200 is provided. Although reference is made hereinbelow to a/the "surgical instrument," it is understood that method 1200 may be performed on one or more surgical instruments for implementation on one or more groups of surgical instruments. Likewise, although reference hereinbelow is made to a/the "storage device," it is understood that method 1200 may be performed using various separate storage media associated with one or more surgical instruments or groups thereof.

Initially, at 1210, a surgical instrument is obtained, e.g., off the manufacturing line, for testing, etc. The surgical instrument is loaded into a test fixture or other suitable test device and, at 1220, is manipulated in a particular manner. The manipulation may include, for example, approximating the jaw members from the open position towards the closed position to achieve a pre-determined jaw force (as measured by the test fixture) and/or pre-determined gap distance between the tissue-contacting surfaces thereof, articulating the end effector assembly a pre-determined amount in a pre-determined direction, deploying the knife blade from the retracted position to the extended position, etc. The input requirements for achieving the manipulation are recoded at 1230. These input requirements are then stored, at 1240, as basis information in a storage device associated with the surgical instrument (e.g., a storage device of the surgical instrument or accessible in conjunction with use of the surgical instrument). The basis information may be the input requirements themselves (e.g., a required rotational input to achieve the manipulation), and/or may include information to enable determination of an input requirement based thereon (e.g., a ratio or formula of the effect of a rotational input towards a desired manipulation to enable use of the basis information for manipulations of varying degree (partially articulated vs full articulated, for example)).

Adjusting information reflecting the effects of use and/or condition of the surgical instrument on the input requirements is determined at 1250 such as, for example, experimentally, via simulation, obtained from other instruments/system, or in any other suitable manner. This adjusting information is likewise stored in the storage device, at 1260. Thus, the surgical instrument is equipped with setting information as well as information to enable adjustment thereof based upon use and/or condition of the surgical instrument. Accordingly, when implemented for use in a surgical procedure, the stored information can be accessed to enable accurate manipulation throughout the useful life of the instrument and in different conditions of the instrument without requiring user input or instrument modification.

Figure 13:
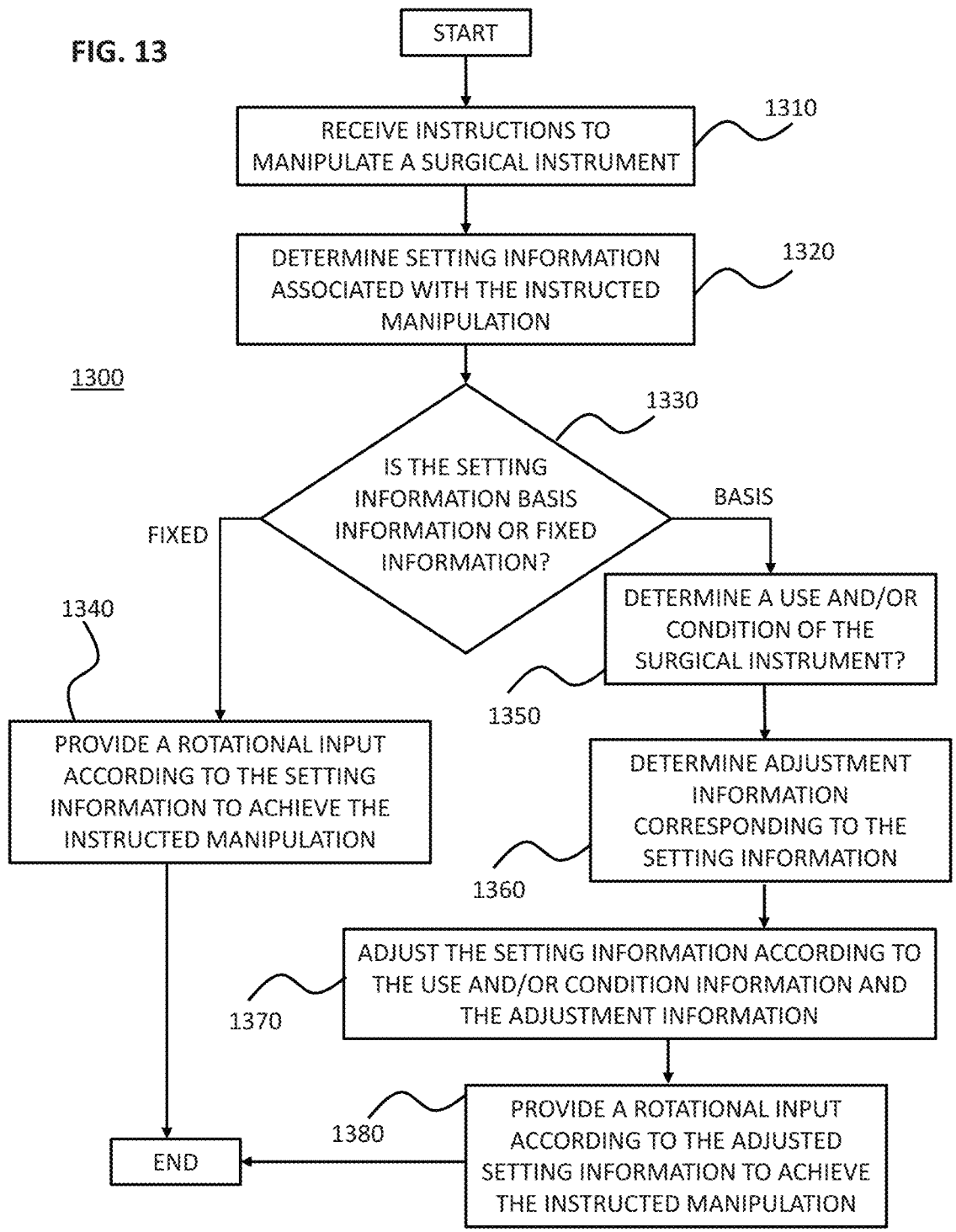

With reference to FIG. 13, a method 1300 of operating a surgical system, e.g., a robotic surgical system, is provided. Initially, at 1310, instructions are received to manipulate a surgical instrument. The instructions may be user input, e.g., via actuation of appropriate mechanical and/or electrical actuators, User Interface (UI) commands, voice commands, etc. or automatic, e.g., based upon feedback, sensed conditions, etc. The manipulation may include, for example, approximating the jaw members from the open position towards the closed position to apply a jaw force suitable for tissue treatment and/or achieve a gap distance between the tissue-contacting surfaces thereof suitable for tissue treatment, articulating the end effector assembly to a desired position, deploying the knife blade from the retracted position to the extended position to cut tissue, etc.

In response to receipt of the instructions, setting information associated with the instructed manipulation is determined at 1320. This setting information may be determined via accessing such information from a storage device associated with the surgical instrument or in any other suitable manner, and may include, for example, a degree of rotational input required to achieve the desired manipulation or information from which the degree of rotational input can be computed, for example.

At 1330, it is determined whether the setting information is basis information of fixed information. If fixed information, meaning the setting information is not subject to adjustment, the setting information is used to provide a rotational input to the surgical instrument to achieve the instructed manipulation. On the other hand, if the setting information is basis information, meaning the setting information is subject to adjustment, a use and/or condition of the surgical instrument is determined at 1350 and adjustment information corresponding to the setting information is determined at 1360. 1350 and 1360 may be performed in any suitable order or simultaneously. The use and/or condition of the surgical instrument may be determined by accessing stored information, based upon feedback data, previous inputs, visual or other tracking information, etc. The adjustment information may be determined by accessing stored information or in any other suitable manner.

Based upon the use and/or condition information and the adjustment information, the setting information is adjusted, if necessary, at 1370. The adjusted setting information is utilized, at 1380 to provide a rotational input to the surgical instrument to achieve the instructed manipulation. Thus, when an instruction to manipulate the surgical instrument is received, the appropriate rotational (or other suitable input) to provide the manipulation is determined, thus accounting for changes of input requirements throughout the useful life of the instrument and in different conditions of the instrument and without requiring user input or instrument modification.

It should be understood that various aspects disclosed herein may be combined in different combinations than the combinations specifically presented hereinabove and in the accompanying drawings. In addition, while certain aspects of the present disclosure are described as being performed by a single module or unit for purposes of clarity, it should be understood that the techniques of this disclosure may be performed by a combination of units or modules associated with, for example, a surgical system.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structures or any other physical structure suitable for implementation of the described techniques. Also, the techniques could be fully implemented in one or more circuits or logic elements.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method, comprising:
   receiving an instruction to manipulate a surgical instrument;
   determining setting information associated with the instructed manipulation;
   determining adjustment information corresponding to the setting information, the adjustment information being correlated with use information including at least one of amount of time or number of events;
   adjusting the setting information using the adjustment information; and
   providing an input to the surgical instrument based upon the adjusted setting information to achieve the instructed manipulation.

2. The method according to claim 1, where in the adjustment information further includes condition information.

3. The method according to claim 2, wherein the condition information includes at least one of a presence of articulation or an amount of articulation.

4. The method according to claim 1, further comprising:
   receiving a second instruction to manipulate the surgical instrument;
   determining second setting information associated with the second instructed manipulation; and
   providing a second input to the surgical instrument based on the second setting information to achieve the second instructed manipulation.

5. The method according to claim 4, wherein the second setting information is unadjusted setting information.

6. A surgical system, comprising:
   at least one input coupler configured to receive an input;
   an end effector assembly;
   an actuation assembly operably coupled between the at least one input coupler and the end effector assembly such that, in response receipt of the input by the at least one input coupler, the end effector assembly is manipulated; and
   a storage device storing setting information and adjustment information, the setting information enabling determination of a first input to the at least one input coupler to achieve a desired manipulation of the end effector assembly, the adjustment information enabling adjustment of the setting information for determination of a second input, different from the first input, to the at least one input coupler to achieve the desired manipulation of the end effector assembly,
   wherein the adjustment information is correlated with use information including at least one of an amount of time or a number of events.

7. The surgical system according to claim 6, wherein the storage device stores the use information.

8. The surgical system according to claim 6, wherein the adjustment information is further correlated with condition information.

9. The surgical system according to claim 8, wherein the condition information includes at least one of a presence of articulation or an amount of articulation.

10. The surgical system according to claim 6, wherein the at least one input coupler is configured to receive a rotational input as the input and to rotate in response thereto.

11. The surgical system according to claim 6, further comprising at least one motor configured to provide the input to the at least one input coupler.

12. The surgical system according to claim 11, further comprising a control device configured to access the setting information and the adjustment information and control the motor based thereon to provide the first input or the second input to achieve the desired manipulation.

13. The surgical system according to claim 12, wherein the control device is further configured to access at least one of use information or condition information and to control the motor based on the setting information, the adjustment information, and the at least one of the use information or condition information to provide the first input or the second input to achieve the desired manipulation.

* * * * *